US00PP12578P2

(12) United States Plant Patent
Stemkens

(10) Patent No.: US PP12,578 P2
(45) Date of Patent: Apr. 23, 2002

(54) VERBENA PLANT NAMED 'SCARLENA'

(75) Inventor: Henricus G. W. Stemkens, Hoorn (NL)

(73) Assignee: Novartis Seeds B.V., Enkhuisen (NL)

( * ) Notice: Subject to any disclaimer, the term of this patent is extended or adjusted under 35 U.S.C. 154(b) by 0 days.

(21) Appl. No.: 09/638,806

(22) Filed: Aug. 14, 2000

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2001/02, Apr. 2, 2001, GTI Jouve Retrieval Software, Citation for Verbena 'Scarlena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its large scarlet flower, early flowering, and a semi-erect habit that becomes spreading as plant develops.

1 Drawing Sheet

BACKGROUND OF THE NEW PLANT

The present invention comprises a new distinct cultivar of Verbena, botanically known as *Verbena×hybrida*. The new cultivar is propagated from cuttings resulting from the cross of 'X813' and 'V480'. 'X813' is a scarlet flowering Verbena having a spreading habit. 'X813' is not commercially available and is not known by any synonyms. 'V480' is a scarlet flowering Verbena having an erect habit. 'V480' is not commercially available and is not known by any synonyms. Neither 'X813' or 'V480' has been patented. As a result of this cross the present cultivar was created in 1994 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed. This new Verbena plant is an annual in most climatical zones in the US, except in zones 8, 9 and 10, where it is a perennial plant.

DESCRIPTION OF THE DRAWING

This new Verbena plant is illustrated by the accompanying photographic drawings, which show blooms, buds and foliage of the plant in full color, the color shown being as true as can be reasonably obtained by conventional photographic procedures.

DESCRIPTION OF THE NEW CULTIVAR

The following detailed descriptions set forth the distinctive charactertistics of this new Verbena. The data which defines these characteristics were collected from asexual reproductions carried out in Enkhuizen, Netherlands. The plant history was taken on 14 weeks old plants, blossomed under natural light in a greenhouse. Color readings were taken in the greenhouse under ambient light. Color references are primarily to The R.H.S. Color Chart of The Royal Horticultural Society of London.

Difference between the new variety 'Scarlena', its parents and a similar cultivar

| Character | 'Scarlena' | 'X813' | 'V480' | 'Temari Scarlet' |
|---|---|---|---|---|
| Flower size | 17–19 mm | 10–12 mm | 21–23 mm | 10–12 mm |
| Earliness | Early | Very late | Early | Very late |
| Seed set | No | No | Yes | No |

The Plant

Classification — Botanical: *Verbena×hybrida*.
Parentage:
*Female parent.*—A seedling named 'X813' is one of our seedlings from our X-generation of plants bred in 1993.
*Pollen parent.*—A seedling named 'V480' is one of our seedlings from our V-generation of plants bred in 1991.
Growth habit: Semi-erect, later spreading.
Plant height: 15–20 cm.
Spreading area of plant: 50–80 cm.
Growth rate: Vigorous.
Strength: Good.
Branching character: Freely branching and lateral branching at every node.
Blooming period: From April until November.

The Stem

Diameter: 2–2.5 mm.
Shape: Tetragonal.
Anthocyan pigmentation: Absent.
Length of internode: 20–60 mm, depending on the light where the plant is propagated.
Pubescence: Slightly pubescent.

The Foliage

Phyllotaxis: Opposite.
Shape of blade: Broadly ovate.

Texture:
*Upper side.*—Smooth.
*Lower side.*—Smooth.
Venation: Pinnate.
Leaf margin: Dentate.
Leaf base: Attenuate.
Leaf apex: Acute.
Length: 35–50 mm.
Width: 26–38 mm.
Depth of incision: 2–3 mm.
Color:
*Upper side.*—Dark green 137A.
*Lower side.*—Light green 137D.
Pubescence: Some pubescence is present.
Length of leaf stem: 5–10 mm.
Petiole surface structure: Slightly pubescent.

The Bud

Peduncle length: 40–70 mm, depending on season.
Size:
*Diameter.*—2 mm.
*Length.*—8–12 mm.
Shape: Elongated and ovate.
Color: Medium green 137C.
Sepals:
*Color.*—Green 137D.
*Form.*—Upright.
*Number.*—5, fused.
*Size.*—8 mm.
*Shape.*—Elongated.

The Flower

Direction: Ascending.
Diameter: 17–19 mm.
Height: 17–19 mm.
Borne: In a cluster.
Form: Salverform; sessile on terminal spikes.
Cluster: Spike.
Color:
*Upper side.*—Red, 45B, a bit brighter.
*Lower side.*—Red, 45B.
Eye: Part of all petals is darker (45A) at the bases The pubescence inside the corolla looks like a small (<1 mm) white eye.
Overlapping of petals: Separate.
No. of petals: 5.
Shape of the petals: Gamopetalos, grown together at the base of the petal. Each petal is heart shaped at the apex.
Petal margin: Entire.
Petal surface texture: Smooth.
Size of the petal:
*Length.*—6–9 mm.
*Width.*—5–7 mm.
Spike:
*Length.*—20–40 mm.
*Diameter.*—40–50 mm.
Calyx: Length of 10–12 mm.
Calyx color: Green141D.
Calyx surface texture: Smooth.
Anthocyanin pigmentation of calyx limb: Absent.
No. of flowers per spike: 25–40.
Fragrance: A very soft rosy-sweet fragrance.
No. of spikes per plant: Whole season: more than 120 spikes per plant.
Lastingness of blooms: New florets continue to open in one spike over a period of 19 days.

Reproductive Organs

One pistil and 4 stamens in pairs; color for both is yellow green 150B. The pistil size is 15–17 mm in length. Pollen is not present. The filaments and anthers are fused to the corolla. The anthers are enclosed and not a prominent feature of the flower. 'Scarlena' does not freely set seed.

Roots

Type of roots: Fibrous. Roots start to grow on every part of the stem that contacts the soil, so not only at the nodes.

Physiological and Ecological Characteristics

Good tolerance to heat and cold. Strong resistance to pests and diseases, particularly powdery mildew.

What is claimed is:

1. A new and distinct variety of Verbena plant, substantially as herein illustrated and described, characterized particularly as to novelty by larger scarlet flowers than other Verbena plants, which appear earlier on the plant, and a growing habit that is first semi-erect, but later spreading and hanging.

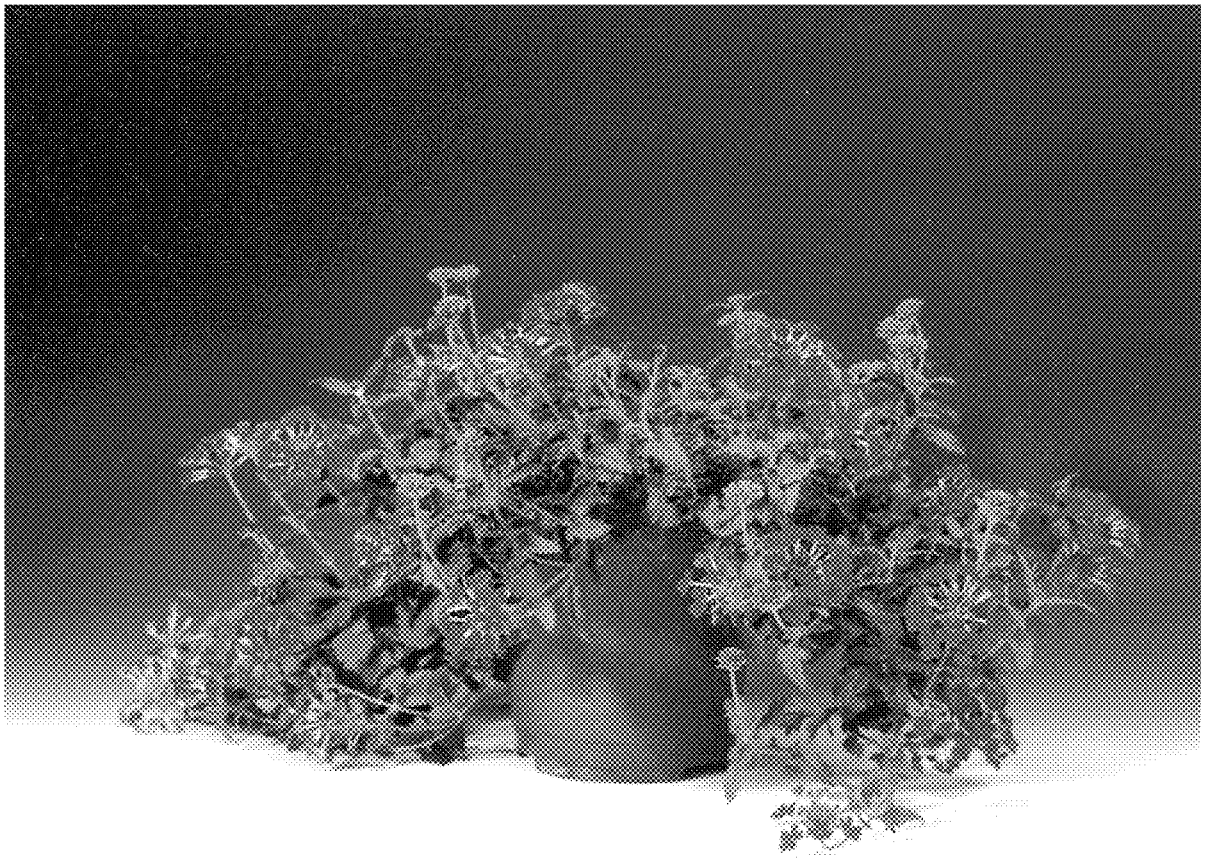

* * * * *